United States Patent [19]

Prasad

[11] 4,412,970
[45] Nov. 1, 1983

[54] PALLADIUM BASED DENTAL ALLOYS

[75] Inventor: Arun Prasad, Cheshire, Conn.

[73] Assignee: Jeneric Industries, Inc., Wallingford, Conn.

[21] Appl. No.: 447,012

[22] Filed: Dec. 6, 1982

[51] Int. Cl.$^3$ .............................................. C22C 5/02
[52] U.S. Cl. .................................. 420/463; 433/200; 433/207
[58] Field of Search ........................ 420/463, 464, 465; 433/207, 200; 148/430

[56] References Cited

U.S. PATENT DOCUMENTS

| | | | |
|---|---|---|---|
| 2,132,116 | 10/1938 | Kiepe | 75/172 |
| 2,143,217 | 1/1939 | Truthe | 75/135 |
| 2,172,512 | 9/1939 | Kilgallon | 75/172 |
| 3,134,671 | 5/1964 | Prosen | 75/172 |
| 3,155,467 | 11/1964 | Yamamoto et al. | 55/16 |
| 3,666,540 | 5/1972 | Burnett | 117/129 |
| 3,819,366 | 6/1974 | Katz | 75/172 R |
| 3,928,913 | 12/1975 | Schaffer | 420/463 |
| 4,123,262 | 10/1978 | Cascone | 75/165 |
| 4,124,382 | 11/1978 | Prosen | 420/463 |
| 4,179,286 | 12/1979 | Knosp | 75/134 N |
| 4,179,288 | 12/1979 | Prosen | 75/172 G |
| 4,205,982 | 6/1980 | German | 75/134 N |
| 4,261,744 | 4/1981 | Boyajian | 420/463 |
| 4,266,973 | 5/1981 | Guzowski et al. | 75/134 N |
| 4,319,877 | 3/1982 | Boyajian | 420/463 |

FOREIGN PATENT DOCUMENTS

| | | |
|---|---|---|
| 510640 | of 0000 | United Kingdom . |
| 1365271 | of 0000 | United Kingdom . |

*Primary Examiner*—L. Dewayne Rutledge
*Assistant Examiner*—S. Kastler
*Attorney, Agent, or Firm*—Kramer and Brufsky

[57] ABSTRACT

A dental alloy for use in porcelain-fused-to-metal restorations including palladium, cobalt, indium, tin, aluminum and rhenium. The aluminum protects the alloy during torch melting and during the porcelain firing process through the formation of a protective oxide. The rhenium provides grain refining for the alloy to increase its elongation, tensile strength, and thus toughness. The alloy must be made under vacuum or in an inert atmosphere to avoid the formation of bubbles in the porcelain during the porcelain firing process.

4 Claims, 2 Drawing Figures

PALLADIUM BASED DENTAL ALLOYS

BACKGROUND OF THE INVENTION

This invention relates to palladium based dental alloys and, in particular, to alloys for use in porcelain-fused-to-metal restorations.

Porcelain-fused-to-metal restorations consist of a metallic sub-structure coated with a veneer of porcelain. Over the years various alloys have been proposed for the sub-structure of these restorations. Many of the early alloys used gold with some platinum or palladium as the main alloy ingredients. However, with the increases and fluctuations in the price of gold and platinum in recent years, other alloys have come to play major roles in this area. One series of alloys which has gained general acceptance is based on nickel, chromium and beryllium as the main ingredients. Another series of alloys, with which this invention is concerned, is based on palladium as the dominant element.

Alloys suitability for use in porcelain-fused-to-metal restorations must satisfy a plurality of demanding conditions. In particular, during torch melting and during the porcelain firing process, the alloy must form a suitable protective oxide. Also, the alloy should not be susceptible to "hot tearing" during the investment casting process.

Of primary importance, the alloy should exhibit good grain structure so as to give it high elongation, tensile strength and toughness. These properties are important in avoiding "hot tearing" and in providing a casting with good burnishability.

Recently, a number of palladium-based commercial alloys, sold under the trademarks CM Metal, Bond-On and Stroma, have become available. In the case of CM Metal and Bond-On, it is believed that the alloys are mixtures of palladium, indium, tin, cobalt, silicon, and, for CM Metal, perhaps some ruthenium. Stroma is believed to be a mixture of palladium, indium, tin and gallium. U.S. Pat. Nos. 4,261,744 and 4,319,877 are believed to relate to the CM Metal alloy. These patents describe alloys consisting of 75-85% by weight of Pd, 5-10% by weight of In, 5-10.5% by weight of Sn, up to 7.5% by weight of Co, Cr or Ni, up to 0.25% by weight of Si, and in the case of U.S. Pat. No. 4,319,877, 0.2-0.7% Ru. U.S. Pat. No. 4,319,877 states that the Ru is added to the alloy as a grain refiner and that the alloy is prepared in a vacuum furnace.

Surprisingly, in seeking to improve the grain structure of alloys similar to the above palladium-based commercial alloys, numerous difficulties were encountered. Specifically, as discussed in detail below, it was found that of the three grain refining elements—rhenium, ruthenium and iridium—only rhenium worked successfully, and then only when the alloy was prepared under vacuum or in an inert atmosphere.

Accordingly, it is one of the objects of this invention to provide a palladium-based dental alloy which is both grain refined and suitable for porcelain-fused-to-metal restorations. In particular, it is an object of this invention to provide a grain-refined palladium based dental alloy which has a low susceptibility to hot tearing. It is a further object of the invention to produce a palladium based dental alloy which forms a suitable oxide during torch melting and during the porcelain firing process.

The attainment of these and other objects of the invention is described below in connection with the description of the preferred embodiments of the invention.

SUMMARY OF THE INVENTION

In accordance with the invention, a palladium based dental alloy is provided which consists essentially of approximately 75-80% by weight palladium, 8-10% by weight cobalt, 0-5% by weight indium, 0-10% by weight tin, 0.05-0.2% by weight aluminum, and 0.15-0.50% rhenium, the total of the constituents being 100%. A preferred embodiment of the alloy has an approximate composition by weight as follows:

TABLE I

| Pd | Co | In | Sn | Al | Re |
|---|---|---|---|---|---|
| 78.2 | 9.5 | 4.0 | 8.0 | 0.1 | 0.2 |

The rhenium serves as a grain refining agent. In accordance with the invention, to introduce this agent, the alloy must be made either in a vacuum or under an inert atmosphere, such as an atmosphere of argon. If not done in this way, the alloy that is produced will cause bubbling of the porcelain during the porcelain firing process. The preferred concentration for rhenium is between about 0.15% and 0.25% by weight.

The aluminum serves to protect the alloy during torch melting and to some extent during the porcelain firing process through the formation of a protective oxide.

DESCRIPTION OF THE PREFERRED EMBODIMENTS

Figure 1:
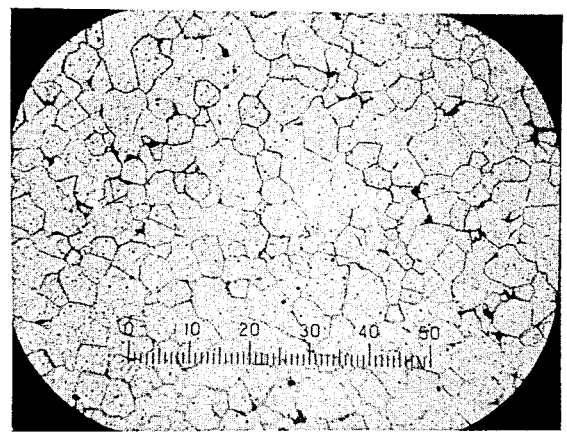
FIGS. 1 and 2 are photomicrographs showing the grain structure of the alloy with and without rhenium as a grain refining agent, respectively.

The alloys of this invention include six constituents: palladium, cobalt, indium, tin, aluminum, and rhenium.

Palladium gives the alloy its basic inertness so that it can withstand the environment of the patient's mouth. Cobalt, indium and tin reduce the alloy's melting point, strengthen it and determine its coefficient of thermal expansion. These components also form an adherent oxide on the surface of the casting which reacts with the porcelain to produce a chemical bond.

The aluminum serves to protect the alloy during torch melting and to some extent during the porcelain firing process. Specifically, as the alloy is torch melted prior to being cast, the aluminum forms an oxide on the outside of the metal. This oxide prevents the absorption of gases by the molten alloy. Such gases, if permitted to be absorbed, could later be released during the porcelain application process and thus form bubbles in the porcelain. Similarly, during the porcelain firing process, the aluminum forms a protective oxide when the metal substructure is heated.

The preferred concentration of aluminum is approximately 0.1% by weight. Higher amounts of aluminum can be used in place of indium and tin to lower the melting point and to strengthen the alloy.

The rhenium component of the alloy provides the important property of grain refining. Alloys consist of individual grains in contact with each other. The size of these grains is critical to the physical properties of the alloy. This size can vary from coarse to fine, and the grains can be regular or irregular.

Ideally, a dental alloy should have fine, regular grains. Alloys with this type of grain structure exhibit superior elongation, tensile strength and toughness properties. Moreover, such alloys are less prone to hot tearing during the investment casting process, as compared to alloys with a coarser grain structure. "Hot tearing", as understood in the art, involves the formation of cracks in the casting due to stresses produced in the casting as it cools in the investment. These cracks can result in failures which necessitate remaking the casting with the concomitant loss of the time, energy and material used to make the original casting.

In an attempt to improve the grain structure of the alloys of this invention rhenium, ruthenium and iridium were tested. It was found that of these elements only rhenium successfully produced a grain refined alloy suitable for use in a porcelain-fused-to-metal restorations, and then only when the alloy was prepared under vacuum or in an inert atmosphere. If the rhenium-containing alloy was prepared in air, the conventional manufacturing technique for precious alloys, the resulting alloy was unsuitable for use in a porcelain-fused-to-metal restoration because it produced bubbles in the porcelain during the porcelain firing process. When the grain refining element iridium was used, only poor grain refinement was achieved regardless of the particular method of preparation employed. This was found to be the case up to and including iridium concentrations as high as 0.5%. When ruthenium was used, it was found that significantly more ruthenium was required to grain refine the alloy than rhenium (approximately 0.4% ruthenium compared to 0.15% rhenium), and the ruthenium alloy produced bubbles in the porcelain even when the alloy was prepared in vacuum or under an inert atmosphere.

Figure 2:
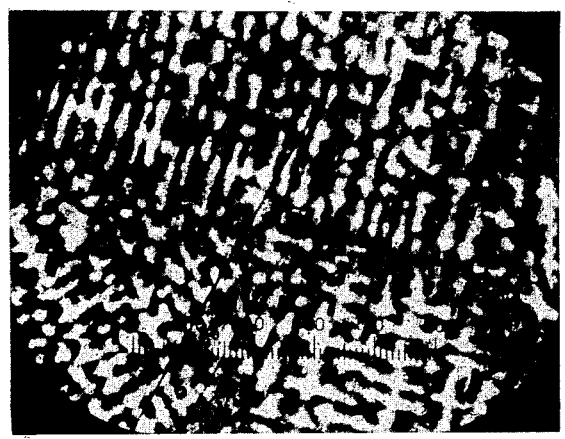

FIGS. 1 and 2 show the effects of grain refining on the alloys of this invention. FIG. 1 is a photomicrograph of the grain structure of an alloy having the composition shown in Table I above. FIG. 2 shows the grain structure when the rhenium is absent and replaced by palladium. As can be seen from these photomicrographs, the grain structure is significantly improved by adding rhenium and the alloy consists of regular, small grains rather than a coarse and dendritic structure.

Table II shows the effect of grain refining on the physical characteristics of the alloy of Table I. In particular, this table shows that by grain refining with rhenium an alloy is produced having increased strength, increased elongation and thus increased toughness. An Instron machine was used to measure the values reported. Alloy A has the composition of the alloy of Table I; alloy B has the same composition but with the rhenium replaced by palladium.

TABLE II

| Alloy | Yield Strength | Ultimate Tensile Strength | Elongation |
| --- | --- | --- | --- |
| Alloy A | 85,000 psi | 105,000 psi | 8% |
| Alloy B | 83,000 psi | 92,000 psi | 6% |

As mentioned above, the standard technique for forming a grain-refined alloy cannot be employed with the alloys of this invention because it leads to the formation of bubbles in the porcelain during the porcelain firing process. In addition to this requirement, the grain refining agent must be introduced within a specific range of concentrations. In particular, at least 0.15% of rhenium must be added to achieve the improved physical properties, and additions above about 0.50% tend to embrittle the alloy.

Although specific embodiments of the invention have been described and illustrated, it is to be understood that modifications can be made without departing from the invention's spirit and scope. Thus, the concentrations of palladium, cobalt, indium, tin, aluminum, and rhenium can be varied from the percentages illustrated and alloys having the superior characteristics of the invention will still result. For example, the palladium concentration can be varied at least between 75 nd 85% by weight; the cobalt concentration between 8 and 10%; the indium concentration between 0 and 5%; the tin concentration between 0 and 10%; the aluminum concentration between 0.05 and 0.2%; and the rhenium concentration between 0.15 and 0.50%.

I claim:

1. A grain-refined palladium based dental alloy for porcelain-fused-to-metal restorations consisting by weight of essentially about 75–80% palladium, 8–10% cobalt, 0–5% indium, 0–10% tin, 0.05–0.2% aluminum and 0.15–0.50% rhenium, the total of the constituents being 100%.

2. The alloy of claim 1 wherein the rhenium concentration is about 0.2%.

3. The alloy of claim 1 wherein the aluminum concentration is about 0.1%.

4. A grain-refined palladium based dental alloy for porcelain-fused-to-metal restorations consisting by weight of essentially about 78.2% palladium, 9.5% cobalt, 4.0% indium, 8.0% tin, 0.1% aluminum, and 0.2% rhenium.

* * * * *